United States Patent [19]

Burns

[11] 3,953,292

[45] Apr. 27, 1976

[54] ENZYMES BOUND TO HEAT-ACTIVATED ATTAPULGITE CLAY

[75] Inventor: Robert A. Burns, Long Valley, N.J.

[73] Assignee: Engelhard Minerals & Chemicals Corporation, Menlo Park, Edison, N.J.

[22] Filed: Jan. 27, 1975

[21] Appl. No.: 544,359

Related U.S. Application Data

[63] Continuation-in-part of Ser. No. 438,563, Feb. 1, 1974, abandoned.

[52] U.S. Cl. .................................. 195/63; 195/68; 195/DIG. 11
[51] Int. Cl.² .......................................... C07G 7/02
[58] Field of Search ................ 195/63, 68, DIG. 11; 210/502

[56] References Cited
UNITED STATES PATENTS

| | | | |
|---|---|---|---|
| 2,717,852 | 9/1955 | Stone | 195/63 X |
| 3,174,826 | 3/1965 | Allegrini et al. | 210/502 X |
| 3,669,841 | 6/1972 | Miller | 195/68 X |

OTHER PUBLICATIONS

McCarter, et al., Thermal Activation of Attapulgus Clay, Industrial and Engineering Chemistry, Vol. 42, No. 3, 1950, pp. 529–533.

*Primary Examiner*—David M. Naff
*Attorney, Agent, or Firm*—Melvin C. Flint; Inez L. Moselle

[57] ABSTRACT

An insolubilized mineral-supported enzyme composite having outstanding catalytic activity and mechanical stability comprises an enzyme covalently attached to silanized porous, attrition-resistant granules of heat-activated attapulgite clay.

12 Claims, No Drawings

ENZYMES BOUND TO HEAT-ACTIVATED ATTAPULGITE CLAY

RELATED APPLICATIONS

This application is a continuation-in-part of my co-pending application, Ser. No. 438,563, filed Feb. 1, 1974, now abandoned.

BACKGROUND OF THE INVENTION

1. Field of the Invention

This invention relates to particulate insolubilized enzyme composites comprising a solid support which can be used and reused as a catalyst to initiate or promote enzyme-catalyzed chemical reaction. More particularly, the invention concerns relatively inexpensive solid-supported insolubilized biochemical catalyst compositions capable of functioning for long periods and useable in continuous processes.

Enzymes are known to be highly active and selective catalysts for many applications involving aqueous solutions of substrate materials. The enzymes are water-soluble protein-like substances. Consequently, when employed in water-soluble form, the enzyme is lost, used up or destroyed to prevent contamination of the ultimate product.

Recently attempts have been made to prolong the activity of enzymes by rendering them insoluble and thus amenable to reuse and recovery by fixing the enzyme upon a water-insoluble support. In the technique of primary interest there is a direct chemical attachment by covalent chemical bonds of the enzyme to an organic polymeric matrix or a porous inorganic solid. Particulate insoluble enzymatically-active enzymes have been produced using solid siliceous support material such as porous glass by reacting the particulate solid siliceous support material with certain organosilanes, e.g., gamma-aminopropyltrimethoxy silane, and attaching an enzyme to the reacted organosilane with a crosslinking agent such as a dialdehyde exemplified by glutaraldehyde. Porous glass particles and nickel-coated screen or other nickel-coated solids are currently the most popular supports, the porous glass being especially preferred because of the high catalytic activity per unit weight of support. Porous glass is, however, very expensive and the cost of enzyme catalysts based upon such support material is prohibitive for many possible industrial applications. Furthermore, porous glass is friable. During catalyst preparation, use and reuse, especially under conditions of strong agitation or high flow rates, the supported catalyst particles are subjected to mechanical forces. When, as in the case of supports based upon porous glass, the particles lack mechanical strength, they tend to break down into fines which are too small to be useful in catalytic reactors because of excessive pressure drops. Breakdown has been reported to result in leaching of the enzyme when it occurs after fixation of enzyme to porous glass.

The widespread industrial usage of insolubilized particulate enzyme catalysts awaits the availability of reasonably low cost products having high catalytic activity and in the form of small granular particles which resist breakdown under dry and wet conditions.

2. Prior Art

The following patents suggest the use of various clays as possible supports for enzyme catalysts wherein the catalyst compositions are obtained by covalently binding enzymes to a silanized support through various crosslinking agents.

U.S. Pat. No. 3,519,538 - R. A. Messing et al - July 7, 1970

U.S. Pat. No. 3,669,841 - R. E. Miller - June 13, 1972

SUMMARY OF THE INVENTION

In accordance with the present invention, insoluble enzymatically active composites in the form of mechanically stable particles comprise sized aggregates (granules) of heat-activated attapulgite clay having a surface area (B.E.T.) in the range of about 100 to 150 $m^2/g.$ and a porosity in the range of about 0.5 to 0.6 ml./g., wherein the pore distribution is such that the major contribution to the total pore volume is derived from pores with radii larger than 500 Angstrom units, and an enzyme coupled to the aggregates by an intermediate silane coupling agent.

The insoluble particulate enzyme catalysts of the invention are characterized by unusually high enzyme activity per unit weight, the activity for any given size particles being of an order obtained with porous glass of similar size. The cost of the enzyme catalyst is a fraction of the cost of a catalyst based upon a porous silica support. In addition to this benefit, the catalysts of the invention are unusually resistant to breakdown in dry form and when slurried in water. Thus the catalysts of the invention maintain their physical form under conditions which may result in breakdown of other granular supported enzyme catalysts. It has been found that simple adsorption will not immobilize common enzymes on granules of heat-activated attapulgite clay. Although the intitial activity of such a supported enzyme catalyst may be high, the catalytic activity may decline rapidly. Presumably this occurs because the enzyme is washed from the substrate.

It will be noted that the support material useful in the practice of the invention has a higher surface area than materials commonly used as supports for enzyme catalysts. Generally materials having surface areas of the order of 40 to 50 $m^2/g.$ are selected as supports for enzyme catalysts in order to avoid any interaction between active sites on the supports and reactants. Porous activated attapulgite clay has been demonstrated to be an outstanding support in spite of the fact that it has a high surface area.

DETAILED DESCRIPTION

An essential feature of the invention resides in the selection of attapulgite clay as the clay support and the use of such clay in the heat-activated (calcined) form. Uncalcined attapulgite clay is not suitable in the practice of my invention for the reason, among others, that granules of uncalcined disintegrate in water and the requisite granular form is not preserved.

Bentonites and kaolins, which constitute the most common clays, are also unsuitable and are therefore outside the scope of the invention. Bentonite can be produced in the form of granules which resist breakdown but such clay granules lack the sorptivity of granules of heat-activated attapulgite clay and do not result in a viable support. Kaolin granules tend to be lacking in mechanical strength and are inadequately sorptive.

The clay particles used in carrying out the invention are obtained by calcining naturally-occurring attapulgite clay (Georgia-Florida fullers earth) at a temperature in the range of 600°F. to 1300°F. for a time sufficient to reduce the volatile matter to a value below 18 percent by weight. The term "volatile matter" (V.M.) is well known in the art. See, for example, U.S. Pat. No. 3,174,826 to Allegrini et al. The naturally occurring clay is commonly called "Attapulgus clay" or "attapulgite" after the predominating mineral constituent. A mined typical sample of such clay containing 70 percent to 80 percent attapulgite, 10 percent to 15 percent other clays, 4 percent to 8 percent quartz and 1 percent to 5 percent calcite or dolomite.

The mineral attapulgite is a hydrated magnesium aluminum silicate, typically about 1 micron long and 0.01 micron wide, with a unique chain structure that imparts to the clay unusual sorptive and colloidal properties. Heat activation results inter alia in loss of all or a substantial proportion of chemically held water (water of crystallization). This heat treatment profoundly affects the physical and chemical properties of the clay. For example, activation results in the collapse of the open channels of the colloidal crystalline attapulgite needles and a rigid porous structure is developed. Heat activation decreases surface area, e.g., typical non-heat treated attapulgite has a B.E.T. surface area of about 210 m$^2$/g. Heat activated attapulgite has a B.E.T. surface area in the range of about 100 to 150 m$^2$/g., typically 125 m$^2$/g. The designation "B.E.T." refers to the nitrogen absorption method described by Brunauer, S., Emmett, P. H. and Teller, E. J., J. AM. CHEM. SOC., 60, 309 (1938) using molecular size data of Livingston, H. K., J. AM. CHEM. SOC. 66, 569 (1944). The effects of heat activation on surface area and porosity of attapulgite clay is discussed by McCarter, W. S. W. et al, IND. ENG. CHEM. 42, 529 (1950).

To prepare the heat-activated clay, the raw clay is crushed and nonclay impurities may be removed. If desired, the raw clay may be extruded in known manner after being mixed with a small amount of water. The raw clay, extruded or not extruded as the case may be, is calcined in suitable equipment, usually a rotary calciner. The calcined crushed clay must be placed in the form of fairly uniform sized granules. For example, the discharge from the calciner may be processed in a corrugated roll mill and the milled clay classified to segregate particles of desired size. Alternatively the clay can be sized before heat activation. Generally, the finer the particles of the calcined attapulgite clay support, the higher the activity of any given enzyme attached thereto. However, as the particles become finer the excessive pressure drop becomes a problem. Consequently, ultrafine particles, e.g., particles finer than 44 microns or 325 mesh, are undesirable. Typical supports are: 500/1000 microns, corresponding to 18/35 mesh, U.S. Standard Sieve; 250/500 microns and 50/100 microns. The designation indicates that essentially all of the particles are larger than the particle size preceding the slash mark and at least as fine as the particle size following the slash and can be within a range of 50 microns to 1000 microns, all sizes being determined by conventional dry screening.

To attach the enzyme covalently to the granules of heat-activated attapulgite clay through an intermediate coupling agent, the clay is silated in known manner to introduce functional groups which may then be linked to the enzyme by crosslinking agents, also known in the art. The disclosure of U.S. Pat. No. 3,669,841 (supra) relative to the silation step, classes and species of substituted organosilanes and crosslinking agents are hereby incorporated by reference. Of the substituted organosilanes, hydrolyzable aminosilanes of the formula given in U.S. Pat. No. 3,669,841 at column 1, lines 72 to 75 are preferred. Especially preferred are omega-aminoalkyl and aminoaryltrialkoxysilanes exemplified by gammaaminopropyltrimethoxysilane, aminopropyltriethoxysilane and aminophenyltriethoxysilane. Examples of preferred crosslinking agents which form a covalent bond with a reactive group on the enzyme that is not essential to the enzyme activity and which also form a covalent bond with a funtional group of the preferred aminosilanes are aldehydes including, for example, formaldehyde, glyoxal, glutaraldehyde and acrolein. Also suitable are bispropiolates and disulfoxyhalides. See U.S. Pat. No. 3,669,841. Another known method for attaching enzymes to inorganic carriers, which is described in U.S. Pat. No. 3,519,538 (supra), may be used and involves covalent attachment of the enzyme through an intermediate organofunctional group. In carrying out this method the clay is silated as in U.S. Pat. No. 3,669,841, using preferably the same type of aminoalkylsilanes to bond the silane to the clay, and then bonding the enzyme to the silanized clay by reacting the amino group of the silane with p-nitrobenzoic acid, reducing the nitro group to the amide and then diazotyzing with nitrous acid. Alternatively, after the hydrolyzable aminoalkylsilane is reacted with the clay granules, the amino group is reacted with thiophosgene to prepare the isothiocyanoalkylsilane derivative. The enzyme is than reacted with the organofunctional portion of the silane coupling agent.

Active enzymes useful in practice of the invention are set forth in U.S. Pat. No. 3,669,841, column 2, line 33 to column 4, line 37, which disclosure is incorporated herein by reference. The enzymes include: the redox enzymes that catalyze oxidation or reduction reactions, e.g., glucose oxidase and catalase; hydrolytic enzymes which hydrolyze proteins and transferase enzymes.

Any inert medium may be used to bond the enzyme, the crosslinking agent and the organosilane which is reacted with sites on the activated clay. Usually an aqueous medium is used. The pH and temperature employed are selected to avoid or minimize deactivation of the enzyme. With most enzymes, the temperature is at room temperature or below.

Generally the enzyme is dissolved in a buffer solution at appropriate pH and temperature and the solution is usually assayed. The silanized clay is added and the glutaraldehyde or other immobilizing agent is added to the slurry. The resulting slurry is maintained at a desired temperature for a suitable time, generally 1 to 72 hours, while maintaining pH at desired level. The bonded enzyme may then be assayed. The bonded enzyme may be stored in water or in a buffered solution at room temperature or below. In some cases the bonded enzyme may be dried mildly prior to use.

Insolubilized enzyme composites of the present invention are useful in analytic and chemical processes using enzymes and are of special value in industrial enzymatic processes carried out in continuously operated columns or stirred tank reactors. In conducting such processes the physical form and mechanical stability of the particulate catalysts of the invention is of utmost value. Industrial processes capable of utilizing the insolubilized enzyme catalysts include, by way of example, starch conversion and sugar processing, dairy processing and brewing.

The following examples illustrate the preparation and utility of enzymatic catalysts of the invention by coupling redox enzymes (glucose oxidase and catalase) to granules of heat-activated attapulgite by means of an intermediate silane coupling agent and using glutaraldehyde as the insolubilizing agent. These examples are given for illustrative purposes and the invention is not to be construed as being limited to the specific embodiments that are illustrated therein.

The clays used in the test were commercial granular grades of heat-activated Attapulgus clay. One was an "RVM" grade and the other an "LVM" grade, these designations referring respectively to regular and low volatile matter contents. Samples of these clays were ground in a hammer mill and sieved to different particle size ranges. Typical properties of these clays are as follows:

|  | RVM-AA | LVM-A |
|---|---|---|
| Free moisture, wt. % loss at 220°F. | 3–7 | 0 |
| Volatile matter, wt. % loss at 1832°F. | 12–16 | 6–10 |
| Surface area, B.E.T., $m^2/g$. | 125 | 125 |

A typical sample of a LVM granular Attapulgus clay has the following pore characteristics:

| Pore Size Distribution | Pore Volume, ml./g. |
|---|---|
| < 10 A radius pores* | 0.005 |
| 11–100 A radius pores* | 0.104 |
| 101–500 A radius pores** | 0.040 |
| > 500 A radius pores** | 0.370 |
| Total | 0.519 |

*determined by $N_2$ adsorption using Isorpta analyzer
**determined by Hg penetration Considering the total pore volume (0.519 ml./g.), most of the pore volume in the calcined clay is contributed by bores with radii > 500 A (i.e., 0.370 ml./g.)

In illustrative examples, glucose oxidase was bonded to samples of the sieved activated attapulgite clay via a gamma-aminopropyl-trioxysilane coupling agent with glutaraldehyde employed as the immobilizing agent. The procedure used for silanizing the clay granules and incorporating the enzyme and couping agent are described in a publication by Herring, Laurence and Kittrell, "IMMOBILIZATION OF GLUCOSE OSIDASE ON NICKEL-SILICA ALUMINA," Biotechnology and Bioengineering, Vol. XIV, pages 975–984 (1972). This procedure was modified by using glutaraldehyde as the immobilizing agent in conventional manner, as described for example in U.S. Pat. No. 3,669,841, Example 3.

Assays of enzyme activity were by the polargraphic technique referred to at page 978 in the publication of Herring et al (supra) using the initial rate of oxygen uptake as the catalyst activity. Glucose was used as the substrate. In making the tests with the immobilized glucose oxidase, 30 mg. of immobilized catalyst was immersed in 1.2 ml. of 5.5 pH citrate phosphate buffer. The solution was saturated with oxygen. A 2M glucose solution (0.12 ml.) was injected into the cell at 25°C. and the suspension was stirred vigorously. After one day the stored samples were assayed. The activity (representing the initial rate of change of oxygen concentration with time) was reported as moles $O_2$/mg. catalyst-sec.

The activities for catalysts prepared with the two different samples of activated attapulgite were essentially the same at all mesh sizes. Consequently, the activity values summarized below in table form represent average values for the two different grades of activated attapulgite clay.

CATALYTIC ACTIVITY OF GLUCOSE OXIDASE COUPLED TO PARTICLES OF HEAT-ACTIVATED ATTAPULGITE CLAY
(−26°C. at pH 5.5)

| Particle size of support, microns | Activity (moles $O_2$ removed per second per mg. of support $\times 10^{-12}$) |
|---|---|
| 500/1000 (granular) | 111 |
| 250/500    " | 270 |
| 125/250    " | 546 |
| 0/125 (powder) | 893 |

The activity values for the glucose oxidase coupled with glutaraldehyde to activated attapulgite clay were compared to values for similarly sized catalysts obtained by immobilizing glucose oxidase on other known supports with glutaraldehyde. In all cases, the catalyst prepared with the heat-activated attapulgite supports were significantly more active than catalyst prepared with supports other than porous glass. For example, the 250/500 micron fraction of a catalyst produced with a support composed of 18 percent nickel oxide of kieselguhr (known to be a support providing high activity for glucose oxidase) was $155 \times 10^{-12}$ moles $O_2$/gm.-sec. This was only about 56 percent of the activity of the catalysts obtained with 250/500 micron particles of heat-activated attapulgite clay. The activity of the 500/1000 micron fraction of the catalyst supported on the nickel-treated kieselguhr was $89 \times 10^{-12}$ moles $O_2$/sec.-mg. as compared to $111 \times 10^{-12}$ for the activated attapulgite clay sample of similar size.

Immobilized catalase samples were prepared using the same procedures employed with the glucose oxidase catalysts. These samples were maintained on a solution buffered at pH 7 (26°C.) and used with a glucose substrate.

Assays of tests made with catalase coupled to various supports were made two days after immobilization. The activity for the catalysts prepared with 250/500 micron attapulgite supports averaged $752 \times 10^{-12}$ moles $O_2$ removed per gram per second. The catalyst supported on nickel-coated kieselguhr (250/500 micron fraction) was $381 \times 10^{-12}$, half that of the attapulgite clay-supported catalyst. At all given mesh sizes, except for the fine powdered samples (0/125 micron) the attapulgite clay-supported catalase catalysts had a higher activity.

I claim:
1. An insolubilized enzymatically active composite in the form of mechanically stable particles comprising sized granules essentially all of which are larger than 50 microns and smaller than 1000 microns of heat-activated attapulgite clay having a volatile matter content below 18% by weight, a surface area in the range of about 100 to 150 $m^2$/g. as determined by the nitrogen absorption method of Brunauer, Emmett and Teller and a porosity in the range of about 0.5 to 0.6 ml./g. wherein the pore distribution is such that the major contribution to the total pore volume is derived from pores with radii larger than 500 Angstrom units, an organosilane coated on the surface of said granules, a crosslinking agent covalently bound to said organosilane and an enzyme covalently bound to said crosslinking agent.

2. The composite of claim 1 wherein said organosilane is an omega-aminoalkyltrialkoxysilane and the crosslinking agent is an aldehyde.

3. The composite of claim 2 wherein the aldehyde is glutaraldehyde.

4. The composite of claim 1 wherein the enzyme is glucose oxidase.

5. The composite of claim 1 wherein the enzyme is catalase.

6. The composite of claim 2 wherein the enzyme is glucose oxidase.

7. The composite of claim 2 wherein the enzyme is catalase.

8. An insolubilized enzymatically active composite in the form of mechanically stabilized particles comprising sized granules essentially all of which are in the range of 50 to 1000 microns of heat-activated attapulgite clay having a volatile matter content below 18% by weight, a surface area in the range of about 100 to 150 m²/g. as determined by the nitrogen absorption method of Brunauer, Emmett and Teller and a porosity in the range of about 0.5 to 0.6 ml./g. wherein the pore distribution is such that the major contribution to the total pore volume is derived from pores with radii larger than 500 Angstrom units, gamma-aminopropyltrioxysilane coated on the surface of said granules, glutaraldehyde covalently bound to said silane and a redox enzyme bound to said crosslinking agent.

9. The composite of claim 8 wherein said redox enzyme is glucose oxidase.

10. The composite of claim 8 wherein said redox enzyme is catalase.

11. The composite of claim 1 wherein said heat-activated attapulgite clay has a volatile matter content in the range of about 6% to 10% by weight and contains no free moisture and the granules have a particle size of about 125 microns to about 250 microns.

12. The composite of claim 1 wherein said heat activated attapulgite clay has a volatile matter content in the range of about 12% to 16% by weight and contains about 3% to 7% free moisture and the granules have a particle size of about 125 microns to about 250 microns.

* * * * *